(12) United States Patent
Kawajiri et al.

(10) Patent No.: US 11,872,334 B2
(45) Date of Patent: *Jan. 16, 2024

(54) PRESSURE DETECTOR

(71) Applicant: Nikkiso Company Limited, Tokyo (JP)

(72) Inventors: Hiroyuki Kawajiri, Shizuoka (JP); Shingo Okamoto, Shizuoka (JP); Ryo Kato, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 610 days.

This patent is subject to a terminal disclaimer.

(21) Appl. No.: 17/093,823

(22) Filed: Nov. 10, 2020

(65) Prior Publication Data

US 2021/0052796 A1 Feb. 25, 2021

Related U.S. Application Data

(63) Continuation of application No. PCT/JP2019/019395, filed on May 15, 2019.

(30) Foreign Application Priority Data

May 16, 2018 (JP) .................................. 2018-094464

(51) Int. Cl.
*A61M 1/16* (2006.01)
*G01L 19/00* (2006.01)

(52) U.S. Cl.
CPC ....... *A61M 1/1605* (2014.02); *G01L 19/0023* (2013.01); *A61M 2205/3331* (2013.01)

(58) Field of Classification Search
CPC ........ A61M 1/1605; A61M 2205/3331; A61M 2205/7536; A61M 1/3641; A61M 1/36; G01L 19/0023

(Continued)

(56) References Cited

U.S. PATENT DOCUMENTS 4,908,493 A 3/1990 Susemihl
5,221,271 A 6/1993 Nicholson et al.
(Continued)

FOREIGN PATENT DOCUMENTS

DE 102008034920 A1 9/2009
EP 0074733 A1 3/1983
(Continued)

OTHER PUBLICATIONS

ITMO20080083A1_Ferrari_NPL.pdf (Year: 2009).*

(Continued)

*Primary Examiner* — Ekandra S. Miller-Cruz
(74) *Attorney, Agent, or Firm* — Young Basile Hanlon & MacFarlane, P.C.

(57) ABSTRACT

A pressure detector is provided that includes a case connectable to a flow route for liquid, and a membrane member attached inside the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion, the pressure detector detecting the pressure of the liquid in the flow route by detecting a pressure in the gas-phase portion with a pressure detection sensor. The pressure detector includes a hydrophobic portion that allows gas to pass through but blocks liquid from passing through, the hydrophobic portion being provided between the gas-phase portion and the pressure detection sensor.

11 Claims, 10 Drawing Sheets

(58) Field of Classification Search
USPC .......................................................... 210/90
See application file for complete search history.

(56) References Cited

U.S. PATENT DOCUMENTS

| | | | |
|---|---|---|---|
| 5,315,877 A * | 5/1994 | Park | ..................... G01L 19/069 73/718 |
| 5,693,887 A * | 12/1997 | Englund | ............. G01L 19/0038 73/756 |
| 6,392,208 B1 | 5/2002 | Arx | |
| 8,092,414 B2 | 1/2012 | Schnell et al. | |
| 8,960,010 B1 | 2/2015 | Crnkovich et al. | |
| 10,775,252 B2 | 9/2020 | Funamura et al. | |
| 2003/0115965 A1 | 6/2003 | Mittelstein et al. | |
| 2007/0118153 A1 | 5/2007 | Funamura et al. | |
| 2007/0295093 A1 | 12/2007 | Reiter et al. | |
| 2009/0071258 A1 | 3/2009 | Kouda et al. | |
| 2010/0186518 A1 | 7/2010 | Jonsson et al. | |
| 2011/0290352 A1 | 12/2011 | Reiter et al. | |
| 2015/0306299 A1 | 10/2015 | Stuva et al. | |
| 2017/0312412 A1 | 11/2017 | Mochizuki | |
| 2017/0340798 A1 | 11/2017 | Lindley et al. | |
| 2020/0198459 A1 | 6/2020 | Bouffier et al. | |
| 2021/0106744 A1 | 4/2021 | Okamoto et al. | |

FOREIGN PATENT DOCUMENTS

| | | | |
|---|---|---|---|
| EP | 0330891 A1 | 9/1989 | |
| IT | MO-20080083 A1 * | 9/2009 | .......... A61M 1/3639 |
| JP | S62-051630 B2 | 10/1987 | |
| JP | H02-001275 A | 1/1990 | |
| JP | H09-024026 A | 1/1997 | |
| JP | 2008-051663 A | 3/2008 | |
| JP | 2008-136673 A | 6/2008 | |
| JP | 2010-172739 A | 8/2010 | |
| JP | 2014-204779 A | 10/2014 | |
| JP | 2015-112223 A | 6/2015 | |
| JP | 2016-221028 A | 12/2016 | |
| JP | 2017-106812 A | 6/2017 | |
| JP | 2019-063439 A | 4/2019 | |
| WO | 2007/040223 A1 | 4/2007 | |
| WO | 2007/120812 A2 | 10/2007 | |
| WO | 2008/106191 A2 | 9/2008 | |
| WO | 2014/028103 A1 | 2/2014 | |
| WO | 2014/093846 A1 | 6/2014 | |
| WO | 2015/099932 A1 | 7/2015 | |
| WO | 2017/015322 A1 | 1/2017 | |
| WO | 2019221202 A1 | 11/2019 | |
| WO | 2019221203 A1 | 11/2019 | |
| WO | 2019221204 A1 | 11/2019 | |
| WO | 2019221205 A1 | 11/2019 | |

OTHER PUBLICATIONS

International Search Report dated Jun. 25, 2019 for Application No. PCT/JP2019/019395 published as WO2019221204.
Potentially related U.S. Appl. No. 15/823,794, filed Nov. 28, 2017 entitled "Medical Liquid-Pressure-Detecting Device", issued as U.S. Pat. No. 10,775,252 on Sep. 15, 2020.
Potentially related U.S. Appl. No. 17/093,817, filed Nov. 10, 2020 entitled "Pressure Detector," Published as WO2019221202.
Potentially related U.S. Appl. No. 17/093,821, filed Nov. 10, 2020 entitled "Pressure Detector," Published as WO2019221203.
Potentially related U.S. Appl. No. 17/093,825, filed Nov. 10, 2020 entitled "Pressure Detector," Published as WO2019221205.
European Search Report for Application No. 19803634.5, dated Apr. 30, 2021.

* cited by examiner

PRESSURE DETECTOR

CROSS-REFERENCE TO RELATED APPLICATION(S)

This application is a continuation of International Application No. PCT/JP2019/019395, filed on May 15, 2019, which claims priority to Japanese Application No. 2018-094464, filed on May 16, 2018, the entire disclosures of which are hereby incorporated by reference.

FIELD

The present invention relates to a pressure detector capable of detecting the pressure of liquid in a flow route by detecting the pressure in a gas-phase portion.

BACKGROUND

In general, dialysis treatment is performed by using a blood circuit for causing blood collected from a patient to extracorporeally circulate and return into the body. Such a blood circuit basically includes, for example, an arterial blood circuit and a venous blood circuit that are connectable to a dialyzer (a blood purifier) including hollow fiber membranes. The arterial blood circuit and the venous blood circuit are provided at distal ends thereof with an arterial puncture needle and a venous puncture needle, respectively. The patient is punctured with the puncture needles, and extracorporeal circulation of blood in the dialysis treatment is thus performed.

To detect the pressure of blood that extracorporeally circulates through a blood circuit, a pressure detector has been proposed as disclosed by PTL 1, for example. The pressure detector includes a case connectable to a blood circuit, and a diaphragm (a membrane member) attached inside the case and with which a liquid-phase portion to be supplied with blood in the blood circuit and a gas-phase portion to be supplied with air are separated from each other, the diaphragm being displaceable in accordance with the pressure of the blood supplied to the liquid-phase portion, the pressure detector being capable of detecting the pressure of the blood by detecting the pressure in the gas-phase portion with a pressure detection sensor. With such a known pressure detector, since the liquid-phase portion and the gas-phase portion are separated from each other by the membrane member, the pressure of the blood in the blood circuit can be detected accurately while the blood is prevented from coming into contact with the air in the gas-phase portion.

PTL 1: Japanese Unexamined Patent Application Publication (Translation of PCT Application) No. 2017-504389 the teachings of which are expressly incorporated by reference herein for all purposes.

SUMMARY

In the above known pressure detector, however, if any problem such as damage to the membrane member or a defect in sealability occurs, the liquid in the liquid-phase portion may leak to the gas-phase portion. In such an event, the leaked liquid may reach the pressure detection sensor and trigger a problem such as a malfunction of the pressure detection sensor.

The present invention has been conceived in view of the above circumstances and provides a pressure detector in which any liquid leaked from a liquid-phase portion to a gas-phase portion can be prevented from reaching a pressure detection sensor.

Variation 1 may comprise a pressure detector that includes a case connectable to a flow route for liquid, and a membrane member attached inside the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion, the pressure detector detecting the pressure of the liquid in the flow route by detecting a pressure in the gas-phase portion with a pressure detection sensor. The pressure detector includes a hydrophobic portion that allows gas to pass through but blocks liquid from passing through, the hydrophobic portion being provided between the gas-phase portion and the pressure detection sensor.

Variation 2 may comprise the pressure detector according to variation 1, the hydrophobic portion is a hydrophobic membrane formed as a membrane.

Variation 3 may comprise the pressure detector according to variation 1 or 2, the gas-phase portion has an opening through which gas is allowed to be introduced into or discharged from the gas-phase portion in accordance with the displacement of the membrane member, and the hydrophobic portion is provided over the opening.

Variation 4 may comprise the pressure detector according to variation 3, a recess is provided around the opening of the gas-phase portion, and the hydrophobic portion is provided over the recess inclusive of the opening.

Variation 5 may comprise the pressure detector according to variation 4, the recess has a contact portion capable of limiting bending of the hydrophobic portion by coming into contact with the hydrophobic portion.

Variation 6 may comprise a blood circuit to which the pressure detector according to any of variations 1 to 5 is connected.

According to variation 1, the hydrophobic portion that allows gas to pass therethrough but blocks liquid from passing therethrough is provided between the gas-phase portion and the pressure detection sensor. Therefore, any liquid leaked from the liquid-phase portion to the gas-phase portion can be prevented from reaching the pressure detection sensor.

According to variation 2, the hydrophobic portion is the hydrophobic membrane formed as a membrane. Therefore, the hydrophobic portion can be easily attached to a desired position between the gas-phase portion and the pressure detection sensor and can be easily processed into a desired shape.

According to variation 3, the gas-phase portion has the opening through which gas is allowed to be introduced into or discharged from the gas-phase portion in accordance with the displacement of the membrane member. Furthermore, the hydrophobic portion is provided over the opening. Therefore, if any liquid leaks from the liquid-phase portion, the leaked liquid can be prevented from reaching the outside of the gas-phase portion.

According to variation 4, the recess is provided around the opening of the gas-phase portion, and the hydrophobic portion is provided over the recess inclusive of the opening. Therefore, the area of the hydrophobic portion where gas is allowed to pass can be set large. Accordingly, the resistance at the passage of the gas through the hydrophobic portion is reduced. Thus, the deterioration in the accuracy of pressure detection by the pressure detection sensor can be suppressed.

According to variation 5, the recess has the contact portion capable of limiting the bending of the hydrophobic portion by coming into contact with the hydrophobic portion. Therefore, if the membrane member that is being displaced toward the side of the gas-phase portion presses and bends the hydrophobic portion, the bent hydrophobic portion can be prevented from closing the opening. Specifically, when the hydrophobic portion bends toward the opening (toward the recess), the hydrophobic portion comes into contact with the contact portion, thereby being prevented from bending further. Hence, a space around the opening (a space in the recess) can be preserved. Accordingly, the opening can be prevented from being closed at the displacement of the membrane member.

According to variation 6, a blood circuit producing the advantageous effects of the pressure detector according to any of variations 1 to 5 can be provided.

DETAILED DESCRIPTION

Embodiments of the present invention will now be described specifically with reference to the drawings.

Figure 1:
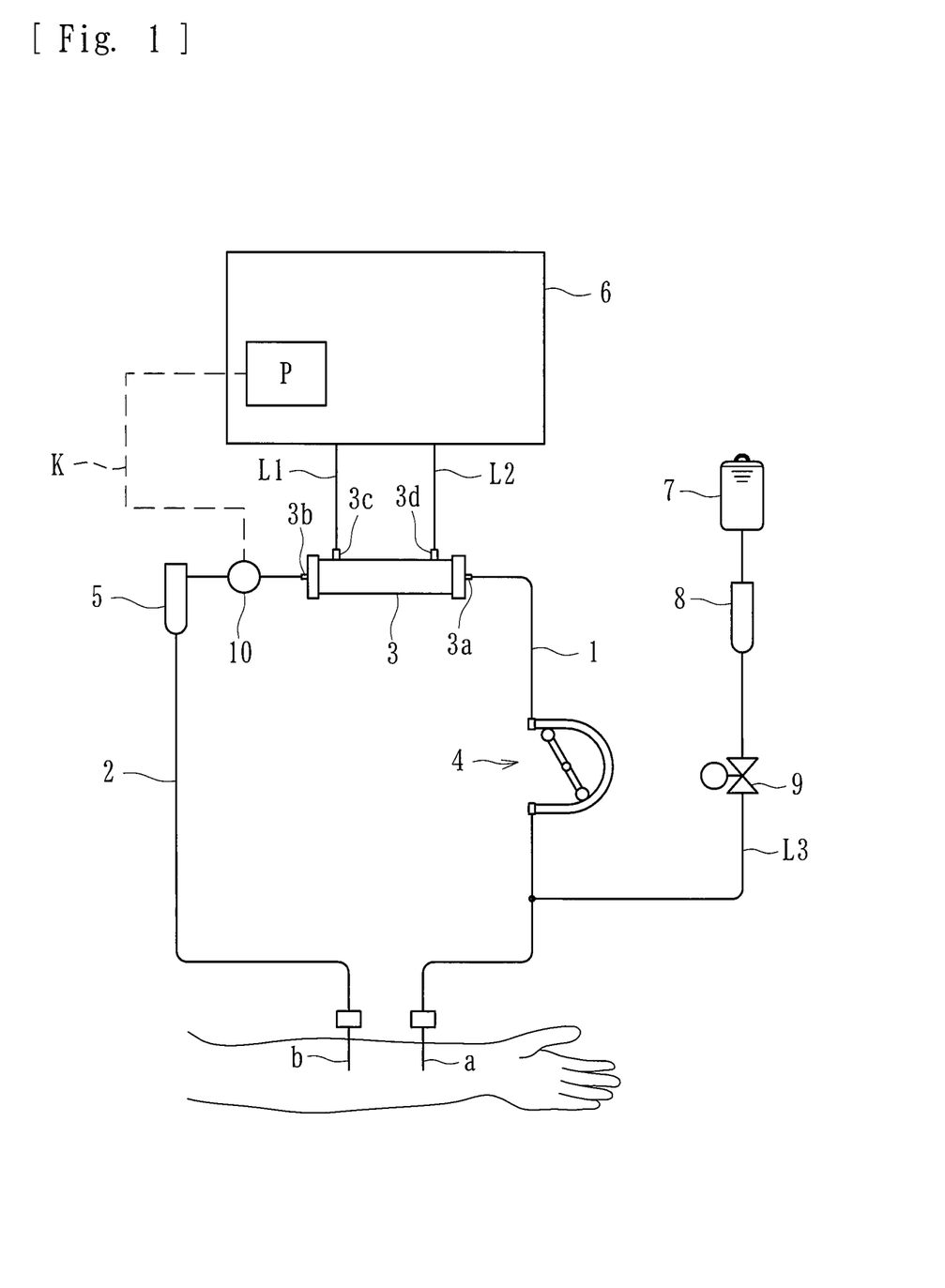
FIG. 1 is a schematic diagram illustrating a dialysis apparatus (a blood purification apparatus) to which a pressure detector according to a first embodiment of the present invention is applied.
Figure 2:
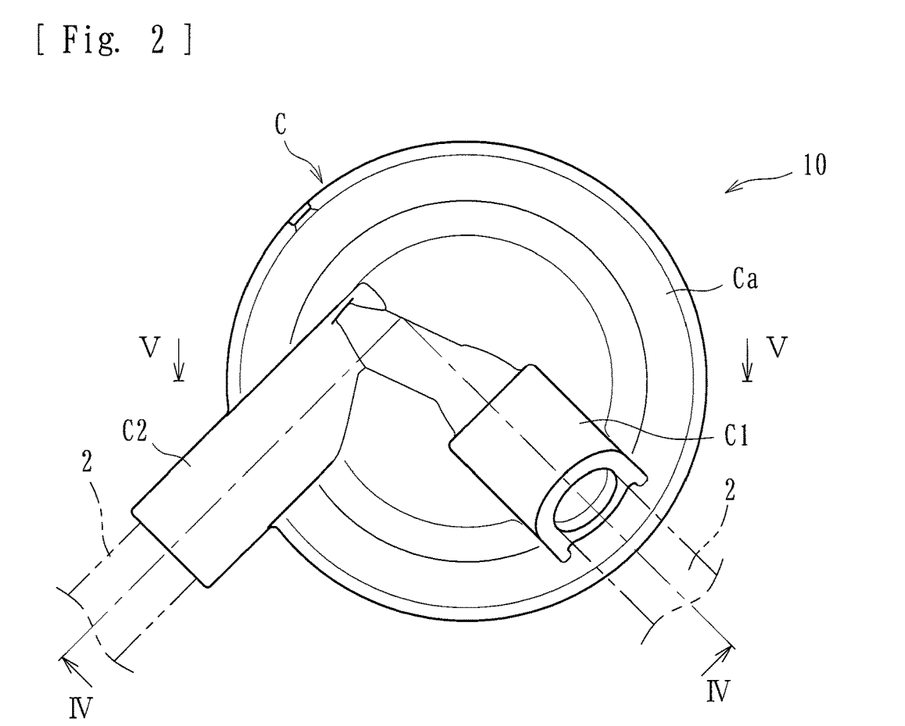
FIG. 2 is a plan view of the pressure detector.
Figure 3:
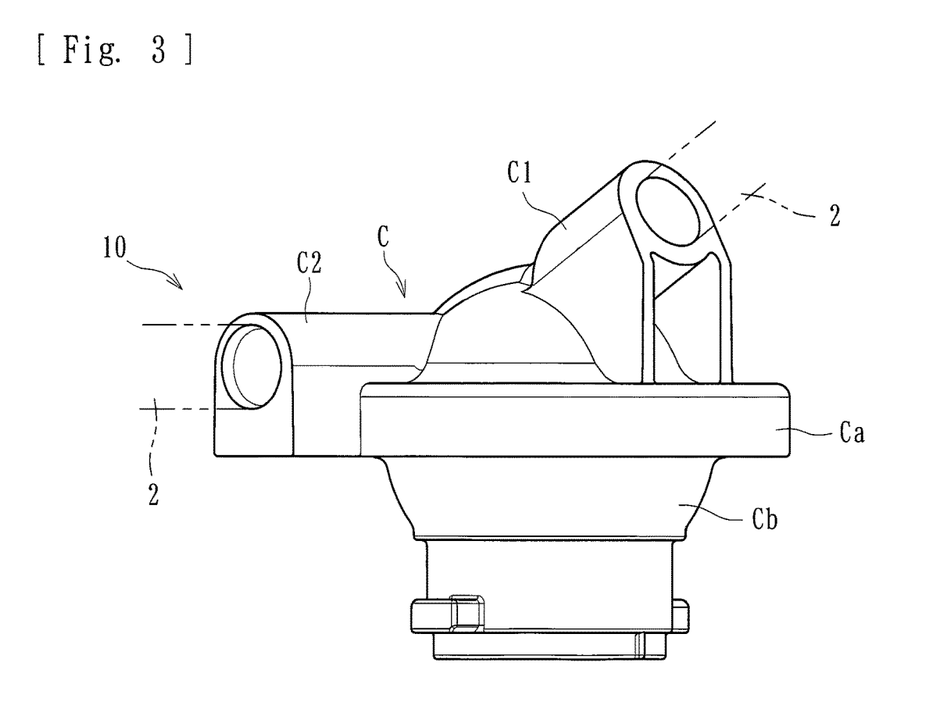
FIG. 3 is a front view of the pressure detector.

A blood purification apparatus applied to a first embodiment is a dialysis apparatus for giving dialysis treatment and basically includes, as illustrated in FIG. 1, a blood circuit including an arterial blood circuit 1 and a venous blood circuit 2, a dialyzer 3 (a blood purifier) provided between the arterial blood circuit 1 and the venous blood circuit 2 and that purifies blood flowing through the blood circuit, a blood pump 4, an air-trap chamber 5 provided to the venous blood circuit 2, a dialysis device 6 that supplies dialysate to the dialyzer 3 and drains waste liquid from the dialyzer 3, a physiological-saline supply line L3 (a substitution-fluid supply line) that allows physiological saline as a substitution fluid to be supplied to the blood circuit, and a storage unit 7 that stores the physiological saline as the substitution fluid.

The arterial blood circuit 1 is provided with an arterial puncture needle (a) connectable to a distal end thereof through a connector, and the blood pump 4, which is of a peristaltic type, at a halfway position thereof. The venous blood circuit 2 is provided with a venous puncture needle (b) connectable to a distal end thereof through a connector, and the air-trap chamber 5 at a halfway position thereof. The air-trap chamber 5 is capable of trapping bubbles in the liquid and is provided with a filtering net (not illustrated), thereby being capable of trapping, for example, thrombi and the like at the time of blood return. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The blood pump 4, which is a peristaltic pump provided to the arterial blood circuit 1, is capable of undergoing normal rotation and reverse rotation and causing the liquid in the blood circuit to flow in the direction of rotation thereof. Specifically, the arterial blood circuit 1 includes a squeezable tube that is softer and has a larger diameter than other flexible tubes forming the arterial blood circuit 1. The blood pump 4 includes rollers for squeezing the squeezable tube in the direction of liquid delivery. When the blood pump 4 is activated, the rollers rotate and thus squeeze the squeezable tube (a portion of the blood circuit), whereby the liquid in the tube can be made to flow in the direction of rotation (the direction in which the rollers rotate).

When the blood pump 4 is activated to undergo normal rotation (leftward rotation in the drawing) while a patient is punctured with the arterial puncture needle (a) and the venous puncture needle (b), the patient's blood flows through the arterial blood circuit 1 and reaches the dialyzer 3, where the blood is purified. Then, the blood flows through the venous blood circuit 2 while undergoing bubble removal in the air-trap chamber 5 and returns into the patient's body. That is, the patient's blood is purified with the dialyzer 3 while being caused to extracorporeally circulate through the blood circuit from the distal end of the arterial blood circuit 1 to the distal end of the venous blood circuit 2. When the blood pump 4 is activated to undergo reverse rotation (rightward rotation in the drawing), the blood in the blood circuit (a portion of the arterial blood circuit 1 that is between the distal end and a position where the blood pump 4 is provided) can be returned to the patient.

The dialyzer 3 has, in a housing thereof, a blood introduction port 3a, a blood delivery port 3b, a dialysate introduction port 3c, and a dialysate delivery port 3d. The blood introduction port 3a is connected to the arterial blood circuit 1. The blood delivery port 3b is connected to the venous blood circuit 2. The dialysate introduction port 3c and the dialysate delivery port 3d are connected to a dialysate introduction line L1 and a dialysate drain line L2, respectively, extending from the dialysis device 6.

The dialyzer 3 houses a plurality of hollow fibers. Spaces inside the respective hollow fibers form flow routes for blood, and spaces between the inner surface of the housing and the outer surfaces of the hollow fibers form flow routes for dialysate. The hollow fibers each have a number of microscopic holes (pores) extending therethrough from the outer surface to the inner surface, thereby forming a hollow fiber membrane. Impurities and the like contained in the blood are allowed to permeate through the hollow fiber membranes into the dialysate.

On the other hand, the dialysis device 6 includes a liquid delivery unit such as a duplex pump provided over the dialysate introduction line L1 and the dialysate drain line L2. A bypass line that bypasses the liquid delivery unit is provided with an ultrafiltration pump for removing water from the patient's blood flowing in the dialyzer 3. One end of the dialysate introduction line L1 is connected to the dialyzer 3 (the dialysate introduction port 3c), and the other end is connected to a dialysate supply device (not illustrated) that prepares a dialysate at a predetermined concentration. One end of the dialysate drain line L2 is connected to the dialyzer 3 (the dialysate delivery port 3d), and the other end is connected to a drainage unit, not illustrated. The dialysate supplied from the dialysate supply device flows through the dialysate introduction line L1 into the dialyzer 3, and further flows through the dialysate drain line L2 into the drainage unit.

The air-trap chamber 5 is provided with an overflow line extending from the top thereof. The overflow line is provided with a clamp unit, such as an electromagnetic valve, at a halfway position thereof. When the clamp unit such as an electromagnetic valve is opened, the liquid (a priming solution or the like) flowing in the blood circuit can be made to overflow through the overflow line.

The physiological-saline supply line L3 (the substitution-fluid supply line) is connected at one end thereof to the arterial blood circuit 1 between the position where the blood pump 4 is provided and the distal end of the arterial blood circuit 1 through a T-shaped pipe or the like. The physiological-saline supply line L3 forms a flow route (such as a flexible tube or the like) through which the physiological saline (the substitution fluid) to substitute for the blood in the blood circuit is allowed to be supplied to the arterial blood circuit 1. The physiological-saline supply line L3 is provided at the other end thereof with the storage unit 7 (a so-called "saline bag"), in which a predetermined amount of physiological saline is stored. The physiological-saline supply line L3 is further provided at a halfway position thereof with an air-trap chamber 8.

The physiological-saline supply line L3 according to the present embodiment is further provided with a clamp unit 9 (such as an electromagnetic valve or the like). The clamp unit 9 is capable of opening and closing the physiological-saline supply line L3, thereby closing and opening the flow route. The state of the physiological-saline supply line L3 is arbitrarily switchable by opening or closing the clamp unit 9, between a closed state where the flow route is closed and an open state where the physiological saline (substitution fluid) is allowed to flow. The clamp unit 9 may be replaced with a general-purpose device such as a pair of forceps with which the flow route of the physiological-saline supply line L3 can be manually closed and opened.

The blood circuit applied to the present embodiment is provided with a pressure detector 10. The pressure detector 10 is connected to the venous blood circuit 2 at a position between the dialyzer 3 and the air-trap chamber 5 and is capable of detecting the pressure of the blood flowing in the venous blood circuit 2 (the blood circuit). Specifically, as illustrated in FIGS. 2 to 6, the pressure detector 10 includes a case C connectable to the flow route for liquid (in the present embodiment, the venous blood circuit 2 (the blood circuit)), and a membrane member M attached inside the case C and with which a liquid-phase portion S1 to be supplied with the liquid in the flow route (in the present embodiment, the blood in the venous blood circuit 2 (the blood circuit)) and a gas-phase portion S2 to be supplied with air are separated from each other, the membrane member M being displaceable in accordance with the pressure of the liquid (blood) supplied to the liquid-phase portion S1. The pressure detector 10 is capable of detecting the pressure of the liquid in the flow route (the venous blood circuit 2) by detecting the pressure in the gas-phase portion S2 with a pressure detection sensor P.

The case C is a hollow molded component obtained by molding a predetermined resin material or the like. The case C is a combination of a liquid-phase-portion case Ca defining the liquid-phase portion S1 and a gas-phase-portion case Cb defining the gas-phase portion S2. The liquid-phase-portion case Ca has an inlet port C1 and an outlet port C2 integrally molded therewith. The inlet port C1 and the outlet port C2 are each connectable to the flow route for liquid and allow the flow route to communicate with the liquid-phase portion S1. The gas-phase-portion case Cb has a connection port C3 integrally molded therewith. The connection port C3 is connectable to one end of a pipe K, to be described below, and allows the one end to communicate with the gas-phase portion S2. The functions of the inlet port C1 and the outlet port C2 of introducing and discharging the liquid may be switched therebetween (that is, the liquid may be discharged from the inlet port C1 while being introduced into the outlet port C2).

Figure 7:
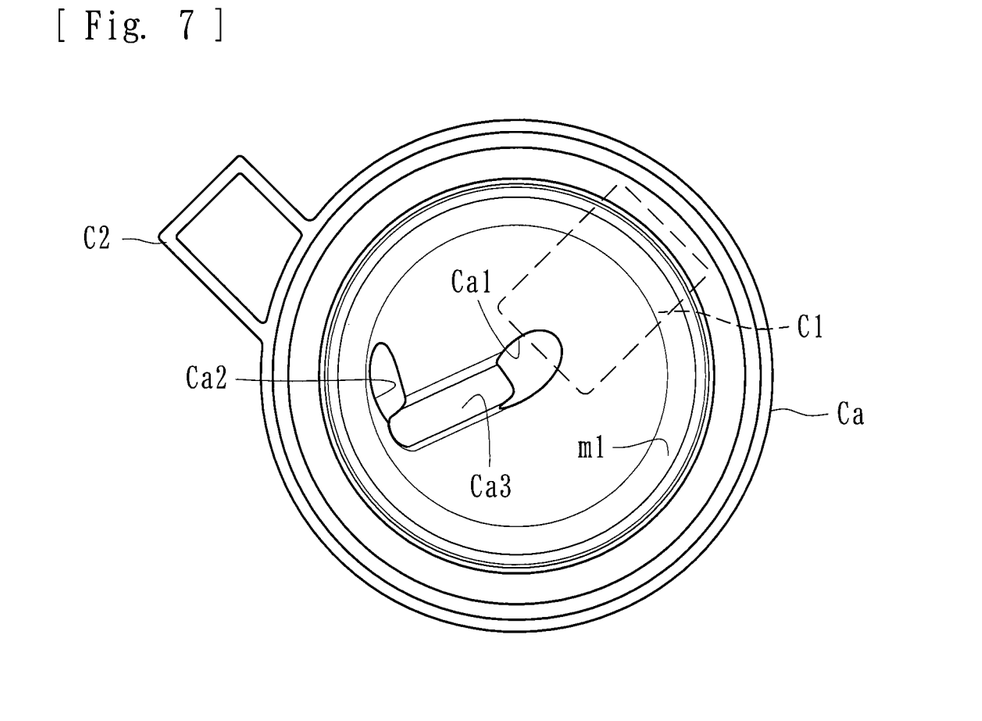
FIG. 7 is a plan view of an inlet opening and an outlet opening provided in a liquid-phase-portion case included in the pressure detector.

The liquid-phase-portion case Ca has an annular holding surface m1 (see FIG. 7) at the periphery thereof. The gas-phase-portion case Cb has an annular holding surface m2 (see FIGS. 8 and 9) at the periphery thereof. When the liquid-phase-portion case Ca and the gas-phase-portion case Cb are mated to each other, a rim Ma of the membrane member M is placed between the holding surface m1 and the holding surface m2. Thus, the membrane member M can be attached in a sealing manner. A space thus provided in the case C is separated (sectioned) by the membrane member M into the liquid-phase portion S1 and the gas-phase portion S2.

Figure 4:
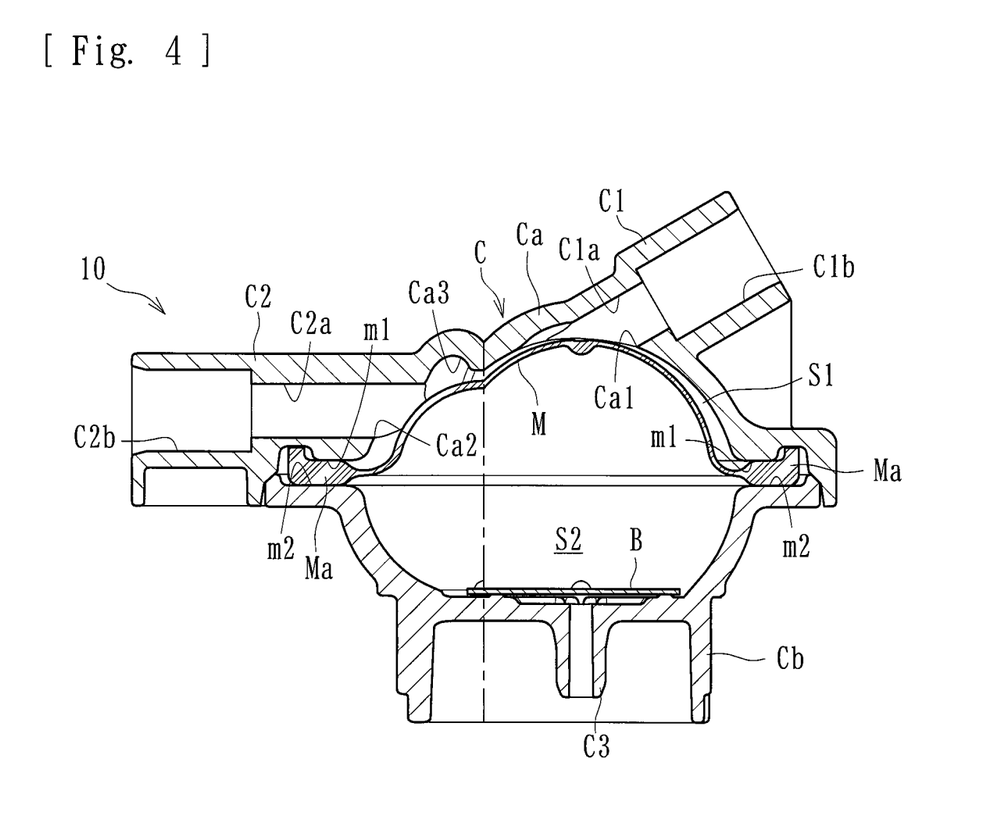
FIG. 4 is a sectional view taken along line IV-IV illustrated in FIG. 2.
Figure 5:
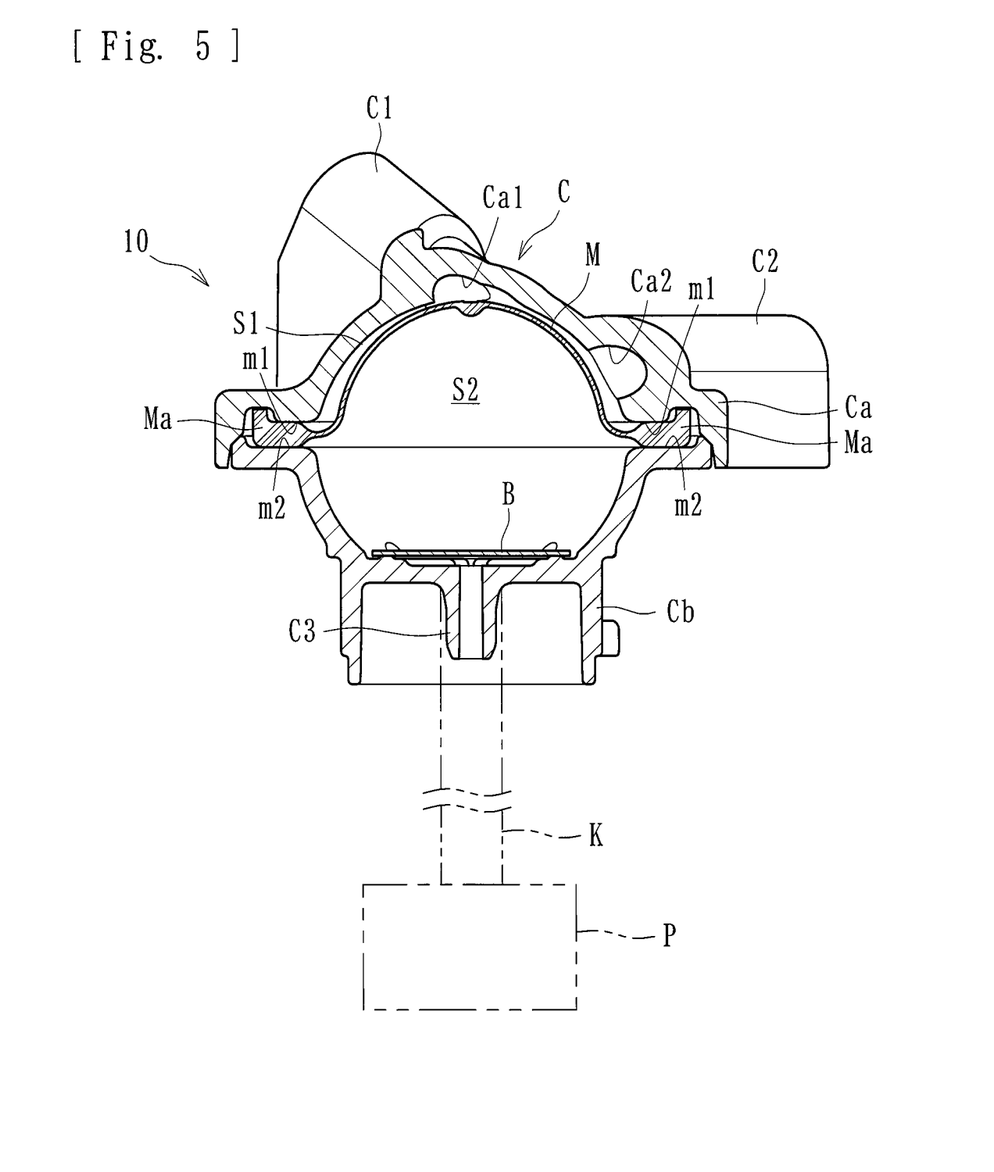
FIG. 5 is a sectional view taken along line V-V illustrated in FIG. 2 (with a membrane member displaced toward the side of a liquid-phase portion).
Figure 6:
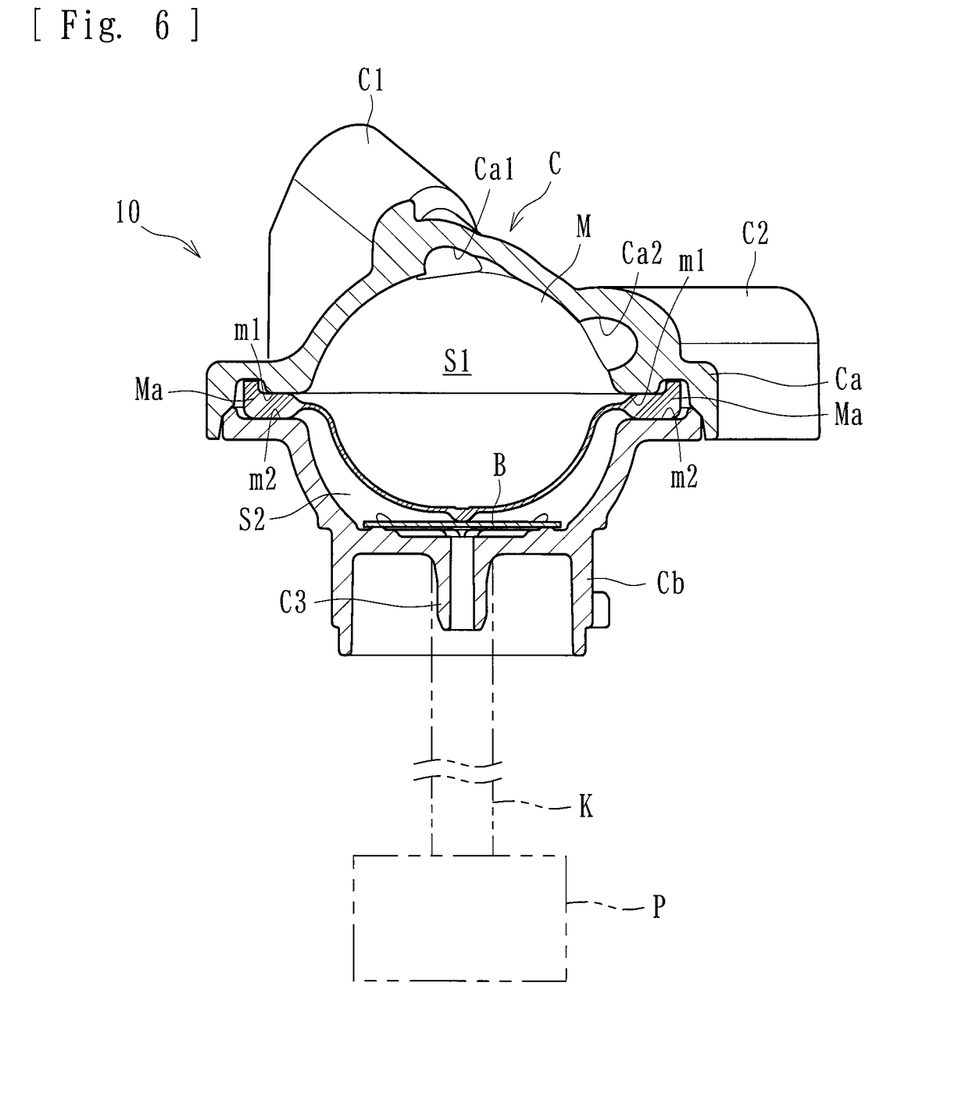
FIG. 6 is a sectional view taken along line V-V illustrated in FIG. 2 (with the membrane member displaced toward the side of a gas-phase portion).

The membrane member M serves as a diaphragm attached inside the case C and is made of a flexible material that is displaceable or deformable in conformity with pressure change occurring in the liquid-phase portion S1 or the gas-phase portion S2. Specifically, if the pressure of the liquid (the hydraulic pressure) in the liquid-phase portion S1 is low, as illustrated in FIG. 4, the membrane member M is displaced toward the side of the liquid-phase portion S1, whereby the capacity of the gas-phase portion S2 is increased. If the pressure of the liquid (the hydraulic pressure) in the liquid-phase portion S1 is high, as illustrated in FIG. 6, the membrane member M is displaced toward the side of the gas-phase portion S2, whereby the capacity of the gas-phase portion S2 is reduced.

The gas-phase-portion case Cb has an opening Cb1 (see FIG. 8) substantially at the center of the bottom thereof. The opening Cb1 provided in the inner surface (the bottom) of the gas-phase-portion case Cb allows the flow route in the connection port C3 and the gas-phase portion S2 to communicate with each other. Accordingly, air (gas) is allowed to be introduced into or discharged from the gas-phase portion S2 in accordance with the displacement of the membrane member M. The pipe K is connected at one end thereof to the connection port C3 and at the other end thereof to the pressure detection sensor P. Therefore, as air (gas) is introduced or discharged through the opening Cb1 with the displacement of the membrane member M, the pressure detection sensor P can detect the pressure in the gas-phase portion S2. Note that the connection port C3 is not limited to the one to be connected to the pipe K and may be connected to another element capable of transmitting the pressure in the gas-phase portion S2 to the pressure detection sensor P.

Figure 8:
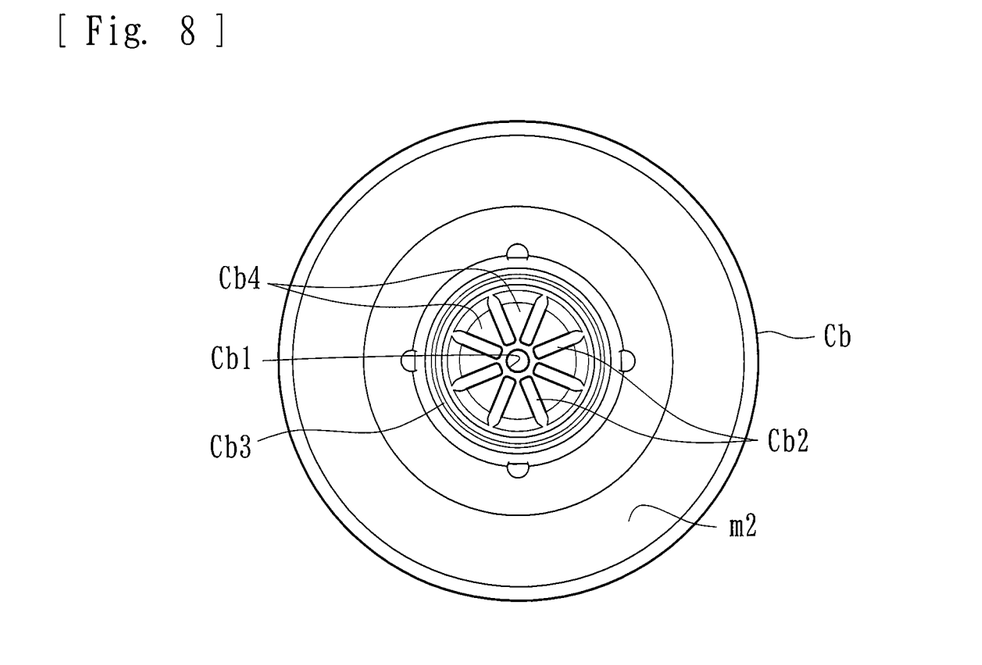
FIG. 8 is a plan view of a gas-phase-portion case included in the pressure detector (with a hydrophobic membrane yet to be attached thereto).
Figure 9:
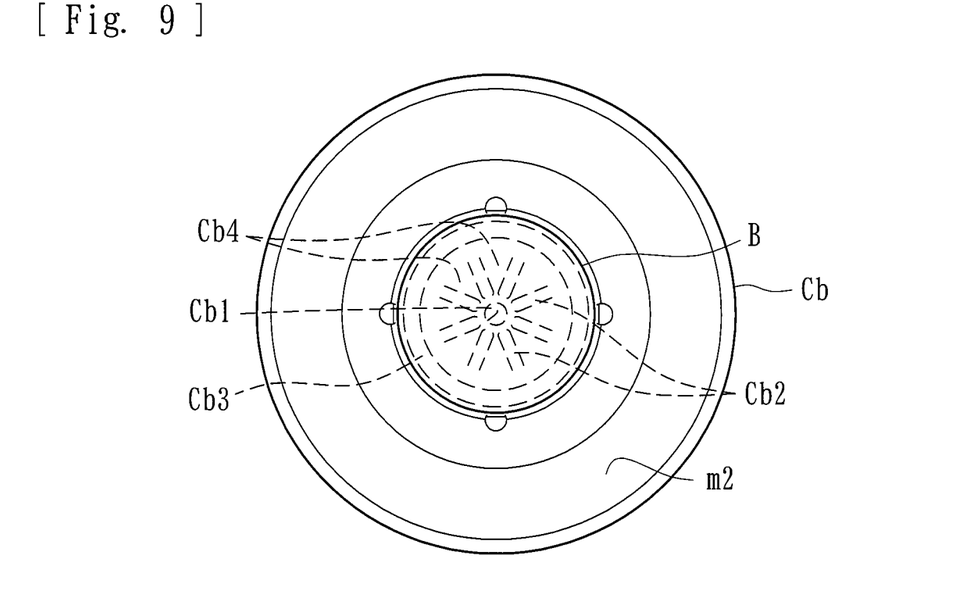
FIG. 9 is a plan view of the gas-phase-portion case included in the pressure detector (with the hydrophobic membrane attached thereto).
Figure 10:
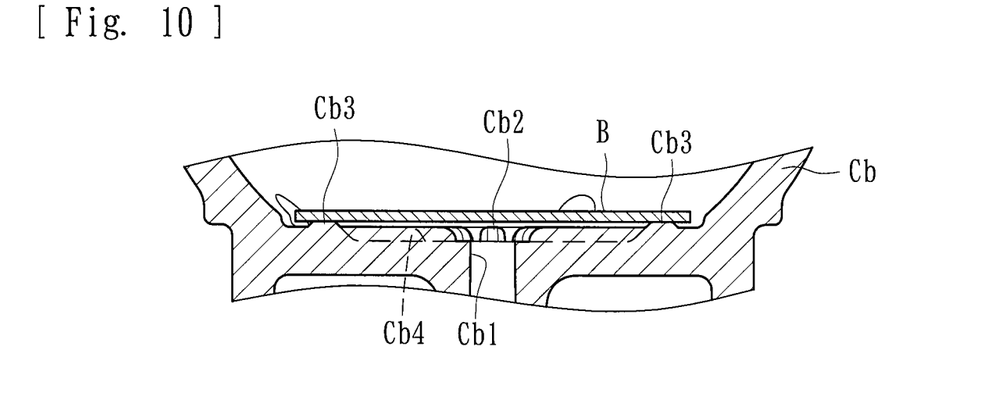
FIG. 10 is a sectional view of part of the pressure detector where the hydrophobic membrane is attached.

The gas-phase-portion case Cb according to the present embodiment has recesses Cb4 surrounding the opening Cb1 provided at the bottom thereof. Furthermore, as illustrated in FIGS. 8 to 10, the gas-phase-portion case Cb is provided with a hydrophobic membrane B (a hydrophobic portion) that covers the recesses Cb4, inclusive of the opening Cb1. The hydrophobic membrane B is provided between the gas-phase portion S2 and the pressure detection sensor P and is formed as a membrane that allows gas to pass therethrough but blocks liquid from passing therethrough. The periphery of the hydrophobic membrane B is welded (for example, by ultrasonic welding or the like) to a ridge Cb3 provided around the opening Cb1.

Figure 11:
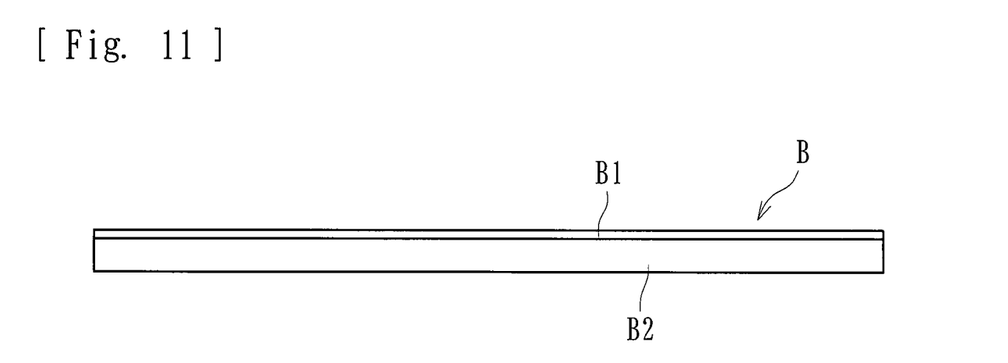
FIG. 11 is a schematic diagram illustrating a section of the hydrophobic membrane included in the pressure detector.

More specifically, as illustrated in FIG. 11, the hydrophobic membrane B according to the present embodiment includes a first layer B1 formed as a sheet (film) of a resin material of PTFE (polytetrafluoroethylene), and a second layer B2 formed as a nonwoven fabric of PEs (polyester) or the like. The first layer B1 and the second layer B2 are stacked in the thicknesswise direction thereof. In the present embodiment, the total thickness of the first layer B1 and the second layer B2 is about 0.1 to 0.5 mm, with the thickness of the first layer B1 (PTFE) being about one tenth of the total thickness.

The hydrophobic membrane B according to the present embodiment is obtained by pasting a sheet of PTFE, which serves as the first layer B1, on the surface of the second layer B2, which serves as a base. Alternatively, another type of hydrophobic membrane M (such as the one including a base made of a different material, or the one including no base) may be employed. The first layer B1 only needs to have a characteristic of allowing gas to pass therethrough but blocking liquid from passing therethrough and may be made of, for example, an acrylic copolymer, polyethersulfone, or the like.

As illustrated in FIG. 8, the recesses Cb4 are defined by a plurality of ribs Cb2 (contact portions) projecting radially about the opening Cb1, so that the bending of the hydrophobic membrane B toward the opening Cb1 can be limited. Specifically, when the hydrophobic membrane B bends toward the opening Cb1 (toward the recesses Cb4), the hydrophobic membrane B comes into contact with the ribs Cb2, thereby being prevented from bending further. Hence, spaces around the opening Cb1 (spaces in the recesses Cb4) can be preserved. Accordingly, the opening Cb1 can be prevented from being closed at the displacement of the membrane member M.

The inlet port C1 according to the present embodiment is a portion (a projected portion) connectable to the flow route for liquid (the blood circuit) and includes, as illustrated in FIG. 4, a flow-route portion C1a through which the liquid (blood) flows into an inlet opening Ca1 (see FIG. 7) of the liquid-phase portion S1, and a connecting portion C1b connectable to the flow route (the blood circuit). Specifically, the flow-route portion C1a and the connecting portion C1b are continuous with each other in the axial direction thereof in the projected portion forming the inlet port C1. When a tube forming the flow route is connected to the connecting portion C1b, the liquid in the flow route can be made to flow into the flow-route portion C1a and then into the liquid-phase portion S1 through the inlet opening Ca1. Note that the inlet port C1 may be shaped as a recess to which the tube forming the flow route is to be connected.

The outlet port C2 according to the present embodiment is a portion (a projected portion) connectable to the flow route for liquid (the blood circuit) and includes, as illustrated in the drawing, a flow-route portion C2a through which the liquid (blood) having flowed into the liquid-phase portion S1 is discharged from an outlet opening Ca2 (see FIG. 7), and a connecting portion C2b connectable to the flow route (the blood circuit). Specifically, the flow-route portion C2a and the connecting portion C2b are continuous with each other in the axial direction thereof in the projected portion forming the outlet port C2. When a tube forming the flow route is connected to the connecting portion C2b, the liquid having flowed into the liquid-phase portion S1 can be made to flow into the flow-route portion C2a and then to be discharged to a flow route (the blood circuit) on the downstream side. Note that the outlet port C2 may be shaped as a recess to which the tube forming the flow route is to be connected.

According to the present embodiment, the hydrophobic portion (hydrophobic membrane B) that allows gas to pass therethrough but blocks liquid from passing therethrough is provided between the gas-phase portion S2 and the pressure detection sensor P (at the position where the opening Cb1 is provided). Therefore, any blood (liquid) leaked from the liquid-phase portion S1 to the gas-phase portion S2 can be prevented from passing through the connection port C3 and the pipe K and reaching the pressure detection sensor P. In particular, the hydrophobic portion according to the present embodiment is the hydrophobic membrane B formed as a membrane. Therefore, the hydrophobic portion can be easily attached to a desired position between the gas-phase portion S2 and the pressure detection sensor P and can be easily processed into a desired shape by cutting or the like.

According to the present embodiment, the gas-phase portion S2 has the opening Cb1 through which gas is allowed to be introduced into or discharged from the gas-phase portion S2 in accordance with the displacement of the membrane member M. Furthermore, the hydrophobic membrane B (the hydrophobic portion) is provided over the opening Cb1. Therefore, if any blood (liquid) leaks from the liquid-phase portion S1, the leaked blood (liquid) can be prevented from passing through the connection port C3 and reaching the outside of the gas-phase portion S2. Furthermore, the recesses Cb4 are provided around the opening Cb1 of the gas-phase portion S2, and the hydrophobic membrane B (the hydrophobic portion) is provided over the recesses Cb4 inclusive of the opening Cb1. Therefore, the area of the hydrophobic membrane B where air (gas) is allowed to pass can be set large. Accordingly, the resistance at the passage of the air through the hydrophobic membrane B is reduced. Thus, the deterioration in the accuracy of pressure detection by the pressure detection sensor P can be suppressed.

Furthermore, the recesses Cb4 have the ribs Cb2 (the contact portions) integrally formed therewith and being capable of limiting the bending of the hydrophobic membrane B by coming into contact with the hydrophobic membrane B. Therefore, if the membrane member M that is being displaced toward the side of the gas-phase portion S2 presses and bends the hydrophobic membrane B, the bent hydrophobic membrane B can be prevented from closing the opening Cb1. Furthermore, according to the present embodiment, a blood circuit producing the above advantageous effects of the pressure detector 10 can be provided.

Figure 12:
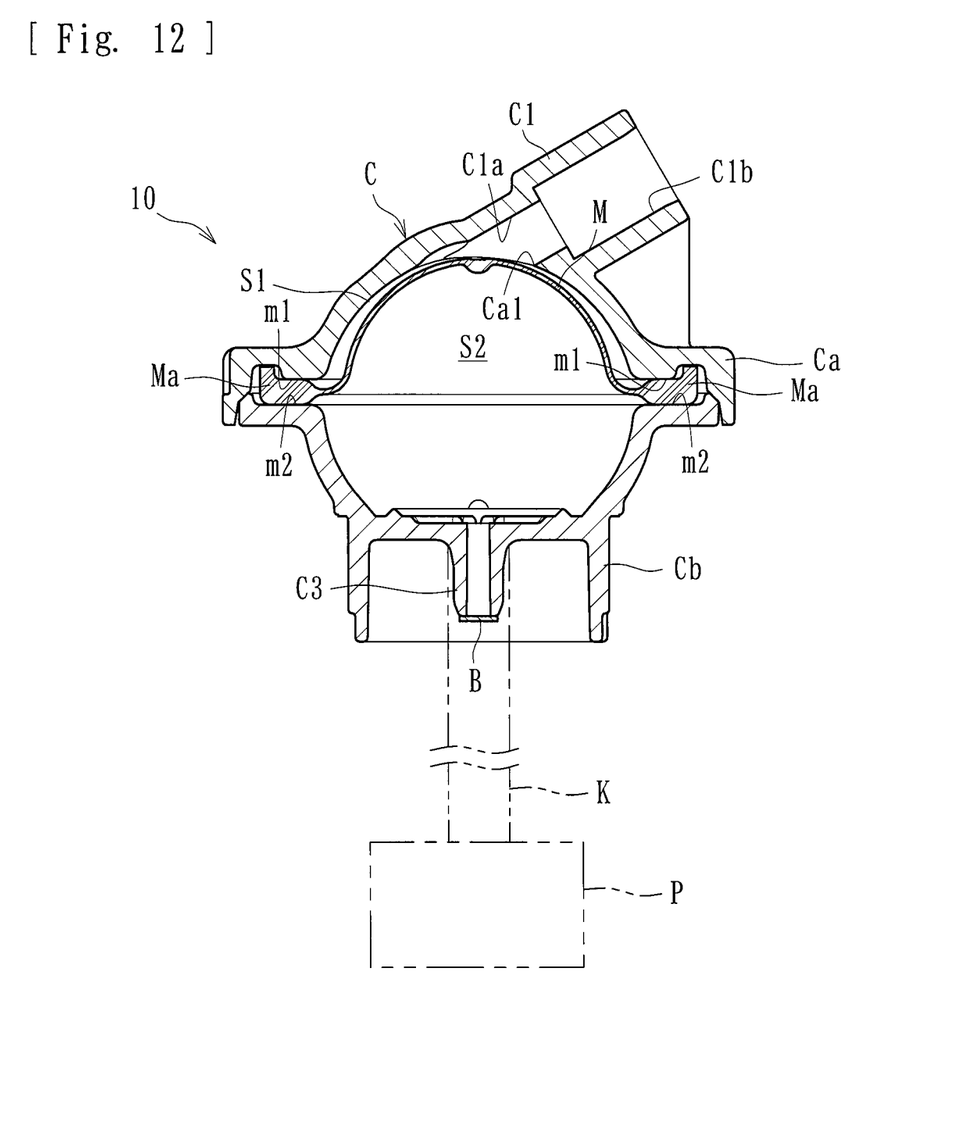
FIG. 12 is a sectional view of a pressure detector according to another embodiment of the present invention (including a hydrophobic membrane attached at an outer opening of a connection port).
Figure 13:
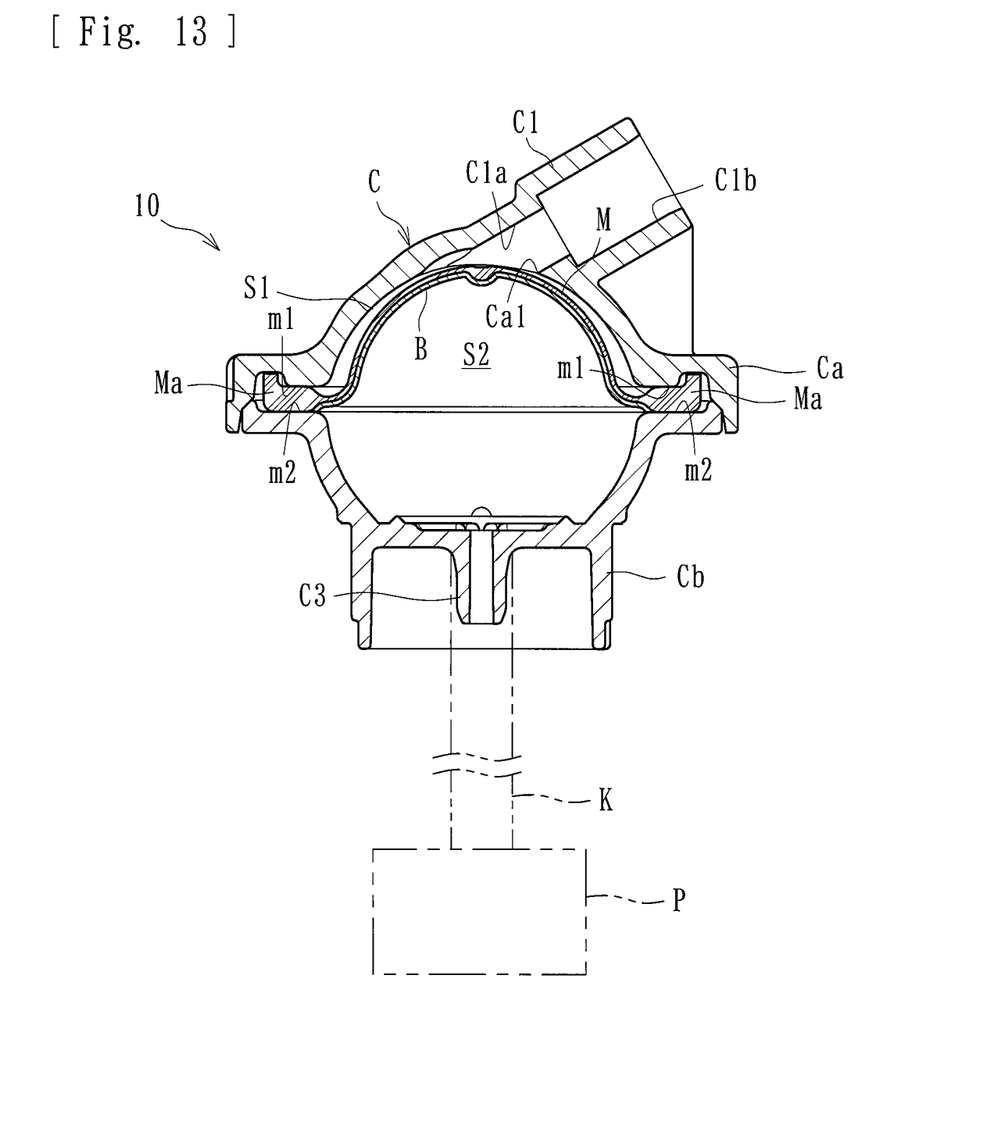
FIG. 13 is a sectional view of a pressure detector according to yet another embodiment of the present invention (including a hydrophobic membrane provided along a membrane member).

While the embodiment has been described above, the present invention is not limited thereto. The hydrophobic membrane B only needs to be provided between the gas-phase portion S2 and the pressure detection sensor P and may be, for example, provided over an outer opening (an opening at the distal end) of the connection port C3 as illustrated in FIG. 12, or along a side of the membrane member M that faces the gas-phase portion S2 as illustrated in FIG. 13 in such a manner as to displace along with the membrane member M.

Figure 14:
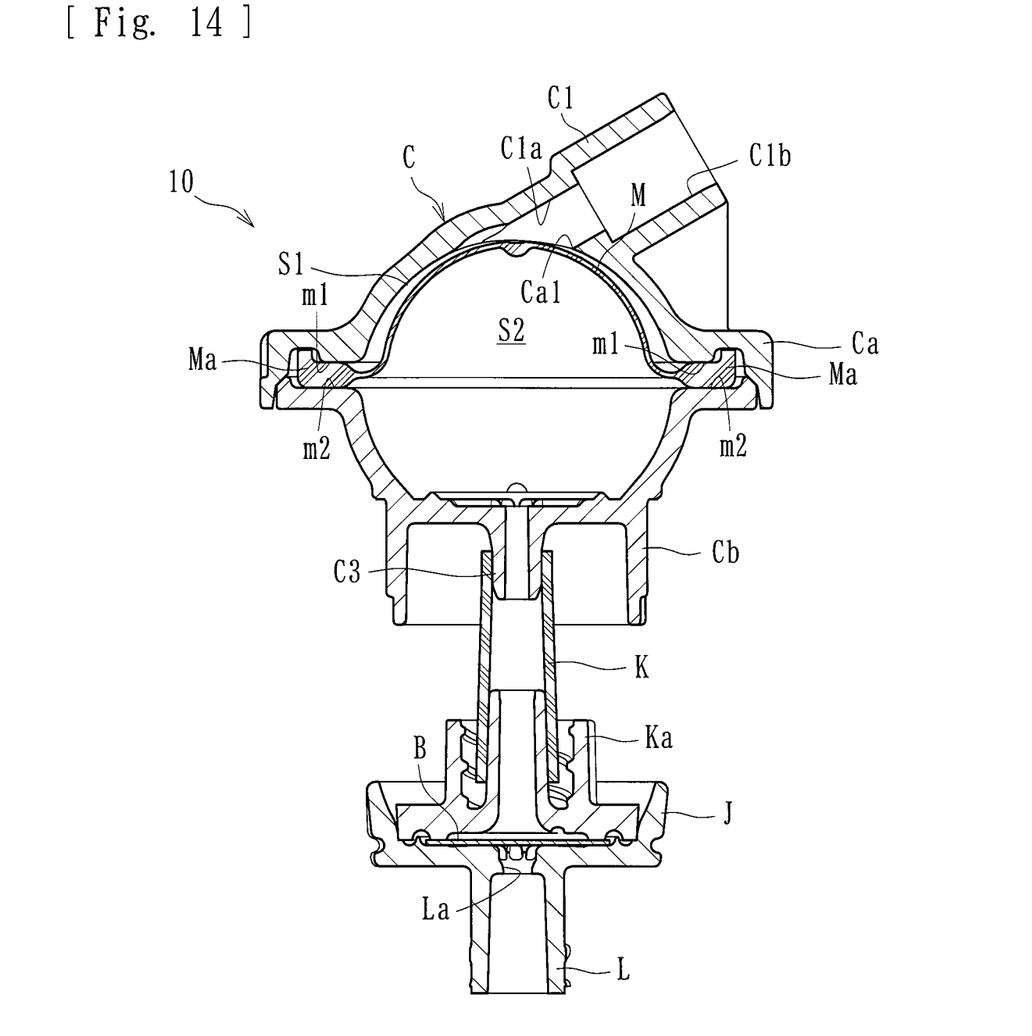
FIG. 14 is a sectional view of a pressure detector according to yet another embodiment of the present invention (including a hydrophobic membrane attached to a connecting portion of the dialysis device).

Alternatively, the present invention may be applied to a configuration illustrated in FIG. 14 that includes a connector Ka provided at an end of the pipe K; a connecting portion J provided on the dialysis device 6 and connectable to the connector Ka; and a pipe portion L extending from the connecting portion J to the pressure detection sensor P, in which the hydrophobic membrane B is provided over an opening La of the pipe portion L, the opening La being provided in the connecting portion J. Needless to say, the hydrophobic membrane B may be provided at a halfway position of a flow route of the pipe K or the pipe portion L. Furthermore, while the above embodiment concerns a case where the plurality of ribs Cb2 (the contact portions) are provided at the bottom (around the opening Cb1) of the gas-phase-portion case Cb, the ribs Cb2 may be omitted or replaced with a contact portion having another shape (such as a ridge or groove having a whirl shape).

Furthermore, while the pressure detector 10 according to the above embodiment is connected to the venous blood circuit 2 at a position between the dialyzer 3 and the air-trap chamber 5, the pressure detector 10 may be connected to another position of the blood circuit (for example, a position of the arterial blood circuit 1 between the distal end and the blood pump 4, or a position of the arterial blood circuit 1 between the blood pump 4 and the dialyzer 3). The blood circuit to which the present pressure detector 10 is to be connected may be of another type. For example, the blood circuit may be provided with not the air-trap chamber 5 but the present pressure detector 10 instead.

While the above embodiment concerns the pressure detector 10 provided to the blood circuit intended for dialysis treatment, the present invention may be applied to a pressure detector provided to another blood circuit to be used in a treatment of purifying blood of a patient. For example, the present invention may be applied to a pressure detector provided to a blood circuit to be used in acetate-free biofiltration (AFBF), continuous slow hemofiltration, hemoadsorption, selective cytapheresis, plasma exchange, double filtration plasmapheresis, plasma adsorption, or the like.

The present invention is applicable to any pressure detector of any other type or for any other use, as long as a hydrophobic portion that allows gas to pass therethrough but blocks liquid from passing therethrough is provided between a gas-phase portion and a pressure detection sensor.

REFERENCE SIGN LIST 1 arterial blood circuit
2 venous blood circuit
3 dialyzer (blood purifier)
4 blood pump
5 air-trap chamber
6 dialysis device
7 storage unit
8 air-trap chamber
9 clamp unit
10 pressure detector
L1 dialysate introduction line
L2 dialysate drain line
L3 physiological-saline supply line
C case
Ca liquid-phase-portion case
Ca1 inlet opening
Ca2 outlet opening
Cb gas-phase-portion case
Cb1 opening
C1 inlet port
C1a flow-route portion
C1b connecting portion
C2 outlet port
C2a flow-route portion
C2b connecting portion
C3 connection port
M membrane member
P pressure detection sensor
S1 liquid-phase portion
S2 gas-phase portion
K pipe
B hydrophobic membrane (hydrophobic portion)
B1 first layer
B2 second layer

The invention claimed is:

1. A pressure detector comprises:
a case connectable to a flow route for liquid,
a membrane member attached inside the case and with which a liquid-phase portion to be supplied with the liquid in the flow route and a gas-phase portion to be supplied with gas are separated from each other, the membrane member being displaceable in accordance with a pressure of the liquid supplied to the liquid-phase portion,
the pressure detector detecting the pressure of the liquid in the flow route by detecting a pressure in the gas-phase portion with a pressure detection sensor, the pressure detector comprising:
a hydrophobic portion that allows gas to pass through but blocks liquid from passing through, the hydrophobic portion being provided between the gas-phase portion and the pressure detection sensor, wherein the hydrophobic portion is a hydrophobic membrane,
an opening, in the gas-phase portion, through which gas is allowed to be introduced into or discharged from the gas-phase portion in accordance with the displacement of the membrane member; and
a recess is provided around the opening of the gas-phase portion, and the hydrophobic portion is provided over the recess inclusive of the opening,
wherein the membrane member and the hydrophobic membrane are located inside of the case.

2. The pressure detector according to claim 1, wherein the recess has a contact portion capable of limiting bending of the hydrophobic portion by coming into contact with the hydrophobic portion.

3. The pressure detector according to claim 1, wherein the gas-phase portion has an opening through which gas is allowed to be introduced into or discharged from the gas-phase portion in accordance with the displacement of the membrane member, and the hydrophobic portion is provided over the opening.

4. A blood circuit to which the pressure detector according to claim 1 is connected.

5. The pressure detector according to claim 1, further comprising:
a ridge located around the opening, wherein the hydrophobic portion has a periphery, and the hydrophobic portion is attached at the periphery to the ridge by a weld.

6. The pressure detector according to claim 1, wherein the membrane member is displaceable into contact with the hydrophobic portion and the hydrophobic portion is pressed by the membrane member toward the opening in the gas-phase portion.

7. A pressure detector comprising: a case connectable to a flow route for liquid, the case comprising: a liquid-phase-portion case and a gas-phase-portion case in communication with the liquid-phase-portion case; a membrane member located between the liquid-phase-portion case and the gas-phase-portion case so that a liquid-phase portion to be supplied with liquid is formed on a side of the membrane member proximate to the liquid-phase-portion case and a gas-phase-portion to be supplied with gas is formed on a side of the membrane proximate to the gas-phase-portion case, wherein the membrane member is displaceable by a pressure of the liquid provided on the side by the liquid-phase-portion; a pressure detection sensor located in communications with the gas-phase-portion to detect the pressure of the liquid in the flow route, the pressure detector comprising: an opening in the gas-phase-portion case that allows gas to be introduced into or discharged from the gas-phase-portion in accordance with the displacement of the membrane member; a recess provided in an interior of the gas-phase-portion case around the opening; and a hydrophobic membrane located within the recess and extending over the opening to allows gas to pass into the flow route and block the liquid from passing into the flow route so that the pressure detection sensor is free of contact with the liquid.

8. The pressure detector according to claim 7, wherein the recess has a contact portion capable of limiting bending of the hydrophobic membrane by coming into contact with the hydrophobic membrane.

9. A blood circuit to which the pressure detector according to claim 7 is connected.

10. The pressure detector according to claim 7, further comprising:
a ridge located around the opening, wherein the hydrophobic portion has a periphery, and the hydrophobic portion is attached at the periphery to the ridge by a weld.

11. The pressure detector according to claim 7, wherein the membrane member is displaceable into contact with the hydrophobic portion and the hydrophobic portion is pressed by the membrane member toward the opening in the gas-phase portion.

* * * * *